US012767925B2

(12) United States Patent
Wei et al.

(10) Patent No.: US 12,767,925 B2
(45) Date of Patent: Oct. 20, 2026

(54) *Cellulosimicrobium cellulans* STRAIN AND USE THEREOF IN STRAW FIELD COMPOSTING

(71) Applicant: Anhui Agricultural University, Hefei City (CN)

(72) Inventors: Zhengyu Wei, Hefei City (CN); Chao Ma, Hefei City (CN); Zhong Yin, Hefei City (CN); Ziyun Zhang, Hefei City (CN); Zhangin Hu, Hefei City (CN); Xin Wang, Hefei City (CN); Shengli Song, Hefei City (CN); Lanshan Jiang, Hefei City (CN); Hongxiang Hu, Hefei City (CN); Zhen Zhang, Hefei City (CN); Xinxin Ye, Hefei City (CN)

(73) Assignee: Anhui Agricultural University, Hefei City (CN)

( * ) Notice: Subject to any disclaimer, the term of this patent is extended or adjusted under 35 U.S.C. 154(b) by 586 days.

(21) Appl. No.: 18/350,084

(22) Filed: Jul. 11, 2023

(65) Prior Publication Data

US 2024/0059624 A1 Feb. 22, 2024

(30) Foreign Application Priority Data

Aug. 16, 2022 (CN) ......................... 202210978768.0

(51) Int. Cl.
*C12N 1/205* (2026.01)
*C05F 11/08* (2006.01)

(52) U.S. Cl.
CPC .............. *C12N 1/205* (2021.05); *C05F 11/08* (2013.01)

(58) Field of Classification Search
None
See application file for complete search history.

*Primary Examiner* — Patricia Duffy
(74) *Attorney, Agent, or Firm* — HoustonHogle LLP

(57) ABSTRACT

The present disclosure provides a *Cellulosimicrobium cellulans* strain and use thereof in straw field composting, belonging to the technical field of microorganisms. In the present disclosure, the *Cellulosimicrobium cellulans* strain is named *Cellulosimicrobium cellulans* MC29-GFP, and is deposited in the China General Microbiological Culture Collection Center (CGMCC), with a deposit number of CGMCC No. 25013. The *Cellulosimicrobium cellulans* MC29-GFP can promote the compost decomposition of straw in field. The experimental results show that the *Cellulosimicrobium cellulans* MC29-GFP significantly increases activities of cellulase and peroxidase in the straw during the decomposition compared with *Bacillus amyloliquefaciens* SQR9, thereby achieving rapid decomposition.

3 Claims, 9 Drawing Sheets

Specification includes a Sequence Listing.

*Cellulosimicrobium cellulans* STRAIN AND USE THEREOF IN STRAW FIELD COMPOSTING

CROSS REFERENCE TO RELATED APPLICATION

This patent application claims the benefit and priority of Chinese Patent Application No. 202210978768.0, filed with the China National Intellectual Property Administration on Aug. 16, 2022, the disclosure of which is incorporated by reference herein in its entirety as part of the present application.

REFERENCE TO SEQUENCE LISTING

A computer readable XML file entitled "SEQUENCE_LISTING.xml", which file has a creation date of Jun. 5, 2026, with a file size of 3207 bytes, contains the sequence listing for this application, has been filed in this application, and is hereby incorporated by reference in its entirety.

TECHNICAL FIELD

The present disclosure belongs to the technical field of microorganisms, and in particular relates to a *Cellulosimicrobium cellulans* strain and use thereof in straw field composting.

BACKGROUND

China is a large agricultural country with abundant crop straw resources, and shows total comprehensive utilization of the straw at about 1 billion tons. Straw turnover is beneficial to improving physical, chemical, and biological properties of the soil, fertilizing the soil, and promoting growth and enhancing yield of the crops. Crop straw is mainly composed of cellulose, hemicellulose, lignin, waxy substances, and a small amount of ash. The hemicellulose and lignin macromolecules with a three-dimensional network structure are filled between crystalline frameworks of the cellulose, and the cellulose, hemicellulose, and lignin are combined in a specific manner to form a stable complex structure. Polysaccharide organic substances such as cellulose and hemicellulose are easily decomposed by microorganisms or enzymes. However, in plant tissues, lignin and hemicellulose are covalently bonded and embed cellulose molecules tightly to form a peripheral matrix. In this way, a strong natural barrier is formed, such that it is difficult for most microorganisms and the degrading enzymes they produce to enter the barrier and decompose the cellulose. Therefore, under natural conditions, the straw has low decomposition rate, incomplete decomposition degree, and poor composting efficiency.

The essence of straw composting is that microorganisms decompose organic matters through metabolic reproduction. Accordingly, a degradation effect of macromolecular organic substances is enhanced by externally adding stalk-decomposing bacteria and increasing the number of microorganisms, thereby promoting the rapid composting of straw. The ability of microorganisms to secrete enzymes is greatly affected by the environment, and different stalk-decomposing bacteria have different effects due to their adaptability to the soil environment where they are used. As a result, it is extremely important to isolate cellulose-degrading bacteria with strong adaptability according to the characteristics of regional environment, so as to improve composting.

Moreover, the effect of nitrogen on straw decomposition mainly affects the composition and activity of straw-decomposing microbial communities by adjusting a carbon/nitrogen (C/N) ratio. A stalk-decomposing agent contains a large number of cellulose- or lignin-degrading bacteria. After this agent is mixed with straw and applied to the soil, the structure and function of soil microbial communities may be changed, thereby changing nitrogen demands. Therefore, an optimal initial C/N ratio of straw turnover may change in the case of combined application of the stalk-decomposing agent. However, there are currently few studies on the comprehensive analysis of the optimal C/N ratio of straw under the application of stalk-decomposing bacteria during the composting.

SUMMARY

In view of this, an objective of the present disclosure is to provide a *Cellulosimicrobium cellulans* strain. The strain can achieve rapid decomposition, and a straw organic fertilizer obtained from the decomposition can increase an output of crops.

To achieve the above objective, the present disclosure provides the following technical solutions:

The present disclosure provides a *Cellulosimicrobium cellulans* strain, where the *Cellulosimicrobium cellulans* strain is named *Cellulosimicrobium cellulans* MC29-GFP, and is deposited in the China General Microbiological Culture Collection Center (CGMCC), with a deposit number of CGMCC No. 25013.

The present disclosure provides a culture method of the *Cellulosimicrobium cellulans* strain, including the following steps: inoculating the *Cellulosimicrobium cellulans* strain into an LB medium to prepare a seed liquid, inoculating the seed liquid into a liquid LB medium, and conducting culture to obtain a bacterial solution; where the bacterial solution has the *Cellulosimicrobium cellulans* strain at a concentration of $1.0\times10^9$ cfu/mL to $2.5\times10^9$ cfu/mL.

The present disclosure provides use of the *Cellulosimicrobium cellulans* strain or a bacterial solution prepared by the culture method in preparation of a straw field composting product.

The present disclosure provides a method for quickly decomposing straw in field, including the following steps: adjusting the straw to a carbon/nitrogen (C/N) ratio of (25-35):1, mixing the straw with a bacterial solution prepared by the culture method, and conducting composting.

Preferably, the C/N ratio of the straw is adjusted by adding a nitrogen source; and the nitrogen source is a urea ammonium nitrate (UAN) solution.

Preferably, the bacterial solution is inoculated at 0.08% to 0.12% of whole compost.

Preferably, the composting is conducted for 57 d to 63 d.

The present disclosure further provides a straw organic fertilizer prepared by the method.

The present disclosure provides use of the *Cellulosimicrobium cellulans* strain or a bacterial solution prepared by the culture method in preparation of a product for promoting plant growth.

Compared with the prior art, the present disclosure has the following beneficial effects.

The present disclosure provides a *Cellulosimicrobium cellulans* strain, where the *Cellulosimicrobium cellulans* strain is named *Cellulosimicrobium cellulans* MC29-GFP, and is deposited in the CGMCC, with a deposit number of CGMCC No. 25013. The *Cellulosimicrobium cellulans* MC29-GFP can promote the compost decomposition of straw in field. The experimental results show that the *Cellulosimicrobium cellulans* MC29-GFP significantly increases activities of cellulase and peroxidase in the straw during the decomposition compared with *Bacillus amyloliquefaciens* SQR9, thereby achieving rapid decomposition.

Deposit of Biological Material

In the present disclosure, the *Cellulosimicrobium cellulans* MC29-GFP was deposited on Jun. 6, 2022 in the China General Microbiological Culture Collection Center (CGMCC), Institute of Microbiology, Chinese Academy of Sciences, at No. 3, Courtyard 1, West Beichen Road, Chaoyang District, Beijing 100101, with an deposit accession number of CGMCC No. 25013.

BRIEF DESCRIPTION OF THE DRAWINGS

FIG. 5A, FIG. 5B, and FIG. 5C are 7 d of CK, SQR9, and MC29-GFP treatments, respectively; and FIG. 5D, FIG. 5E, and FIG. 5F are 60 d of CK, SQR9, and MC29-GFP treatments, respectively);

(FIG. 6A: cellulase at 7 d and 60 d; FIG. 6B: peroxidase at 7 d and 60 d); FIG. 7B, a relative abundance of the dominant microflora at 60 d).

Figure 1A:
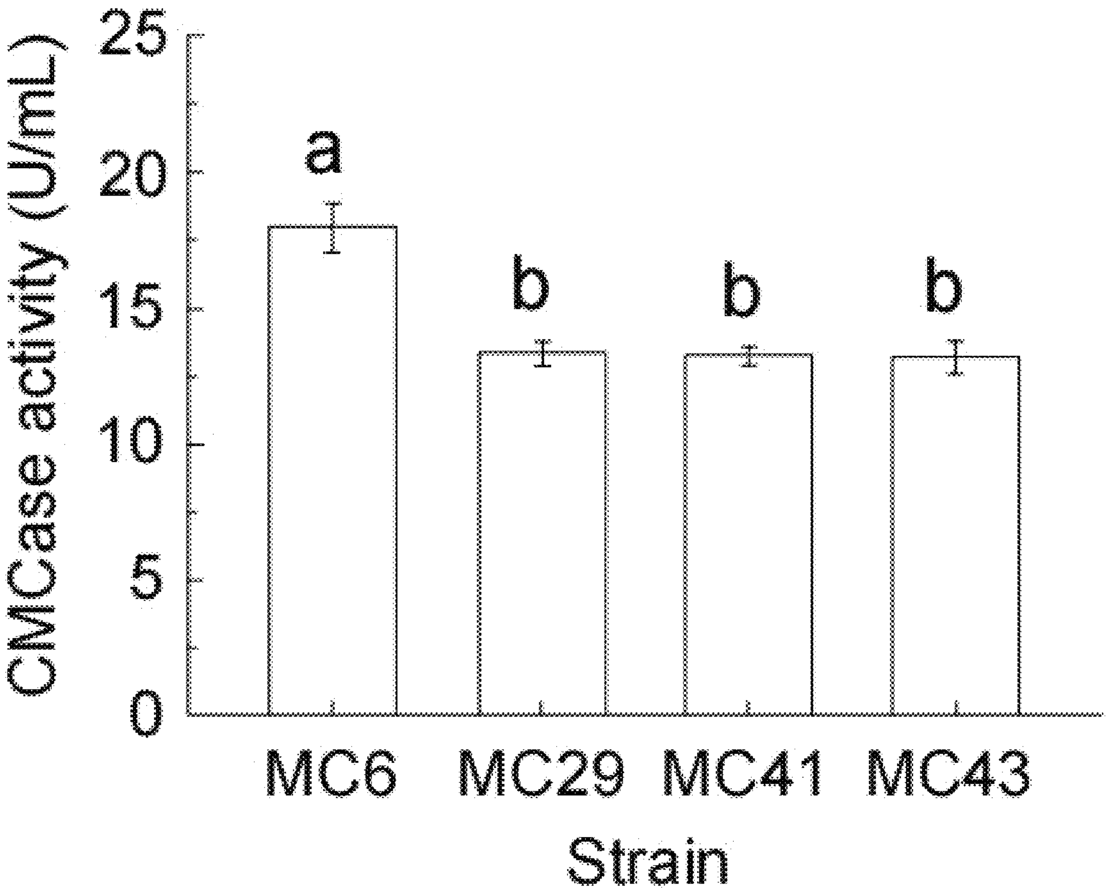
FIGS. 1A-B show an ability of 4 strains in carboxymethyl cellulase (CMCase) production and indoleacetic acid (IAA) secretion.

"MC29" in FIGS. 1A-B to FIGS. 7A-B are all "MC29-GFP".

DETAILED DESCRIPTION OF THE EMBODIMENTS

The present disclosure provides a *Cellulosimicrobium cellulans* strain, where the *Cellulosimicrobium cellulans* strain is named as *Cellulosimicrobium cellulans* MC29-GFP, and is deposited in the CGMCC, with a deposit number of CGMCC No. 25013, as described above in the section entitled DEPOSIT OF BIOLOGICAL MATERIAL.

In the present disclosure, the *Cellulosimicrobium cellulans* strain is derived from Shajiang black soil in the long-term straw returning test plot of the Agricultural Demonstration Science and Technology Park in Mengcheng County, Anhui Province. The strain has the following morphological characteristics: colonies are yellow, have a smooth and moist surface, with neat edges, and are irregularly arranged and densely distributed; individual strains are rod-shaped without flagella.

The present disclosure provides a culture method of the *Cellulosimicrobium cellulans* strain, including the following steps: inoculating the *Cellulosimicrobium cellulans* strain into an LB medium to prepare a seed liquid, inoculating the seed liquid into a liquid LB medium, and conducting culture to obtain a bacterial solution; where the bacterial solution has the *Cellulosimicrobium cellulans* strain at a concentration of $1.0\times10^9$ cfu/mL to $2.5\times10^9$ cfu/mL.

The present disclosure provides use of the *Cellulosimicrobium cellulans* strain or a bacterial solution prepared by the culture method in preparation of a straw field composting product.

The present disclosure provides a method for quickly decomposing straw in field, including the following steps: adjusting the straw to a carbon/nitrogen (C/N) ratio of (25-35):1, preferably 35:1, mixing the straw with a bacterial solution prepared by the culture method, and conducting composting.

In the present disclosure, the C/N ratio of the straw is preferably adjusted by adding a nitrogen source; the nitrogen source is preferably a UAN solution, which includes 3 forms of nitrogen, namely amide nitrogen, ammonium nitrogen, and nitrate nitrogen, thus taking into account the optimal nitrogen source of the MC29-GFP strain and the requirement of rapid release of nitrogen during the straw decomposition.

In the present disclosure, the bacterial solution is inoculated at preferably 0.08% to 0.12%, more preferably 0.1% of whole compost; and the composting is conducted for preferably 57 d to 63 d, more preferably 60 d.

The present disclosure further provides a straw organic fertilizer prepared by the method.

The present disclosure provides use of the *Cellulosimicrobium cellulans* strain or a bacterial solution prepared by the culture method in preparation of a product for promoting plant growth.

The technical solutions provided by the present disclosure will be described in detail below with reference to examples, but the examples should not be construed as limiting the claimed scope of the present disclosure.

Example 1

Screening and Identification of *Cellulosimicrobium cellulans* Strain MC29-GFP

1. Fresh samples of Shajiang black soil collected from the long-term straw returning test plot of the Agricultural Demonstration Science and Technology Park in Mengcheng County, Anhui Province were crushed and sieved. 10 g of the sample was added to a 250 mL Erlenmeyer flask, added with 90 mL of sterile water, shaken in a shaker for 30 min at 28° C., 150 r/min, and then allowed to stand for 15 min. A small amount of an obtained soil suspension was diluted to 0.1 mg/L, spread evenly on an LB agar plate, serially diluted and cultured at 30° C.±2° C. to isolate strains, which were further purified. A cellulose degrading ability of the strain was determined by qualitative analysis of a transparent circle on a CMC selection medium.

After the qualitative analysis, four strains were selected, including: MC6, MC29-GFP, MC41, and MC43.

2. Determination of CMCase Activity and IAA Secretion Ability

The 4 strains obtained by screening were inoculated in a LB liquid medium and cultured with shaking for 8 h (36° C., rotating speed: 200 r/min). 1 mL of a resulting culture solution was added into a liquid medium with corn straw powder as a sole carbon source to culture for 60 h, and then centrifuged at a low temperature for 10 min (4° C., 5,000 r/min). 0.2 mL of an obtained supernatant was added with 1.8 mL of a 1% CMC-Na solution and treated in a water bath at 50° C. for 30 min, 3.0 mL of a DNS reagent was added, and then a mixture was treated in boiling water bath for 5 min. The reaction was terminated to conduct color developing, and $OD_{520}$ to was determined to obtain the CMCase activity.

IAA secretion ability: the 4 strains were cultured in an LB liquid medium containing L-tryptophan (100 mg/L) with shaking for 24 h (36° C., 200 r/min). An obtained bacterial suspension was centrifuged to prepare a supernatant, which was added into an equal volume of a Salkowski colorimetric solution and allowed to stand for 30 min, and $OD_{530}$ was determined to obtain an IAA concentration. The IAA contents of the 4 strains were shown in FIG. 3.

Figure 1B:
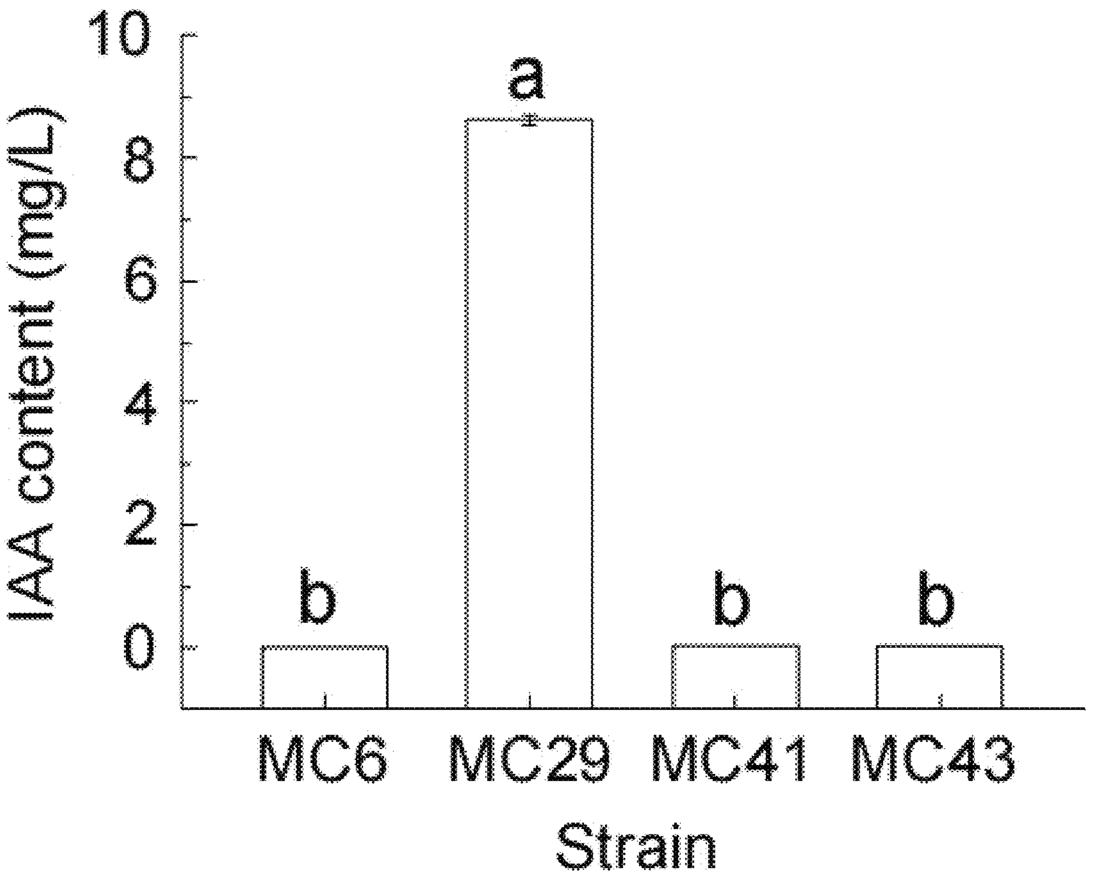

As shown in FIGS. 1A-B, the MC29-GFP strain had the strongest ability to secrete IAA, at a concentration reaching 8.63 mg/L, which was significantly higher than that of other strains.

3. Morphological Identification of MC29-GFP

The morphological identification and study on physiological and biochemical characteristics of MC29-GFP were conducted with reference to "Bergey's Manual of Determinative Bacteriology" (8th edition) and "Common Bacterial System Identification Manual". The strain MC29-GFP had a colony morphology shown in FIGS. 1A-B, and Gram staining shown in FIG. 2.

Figure 2:
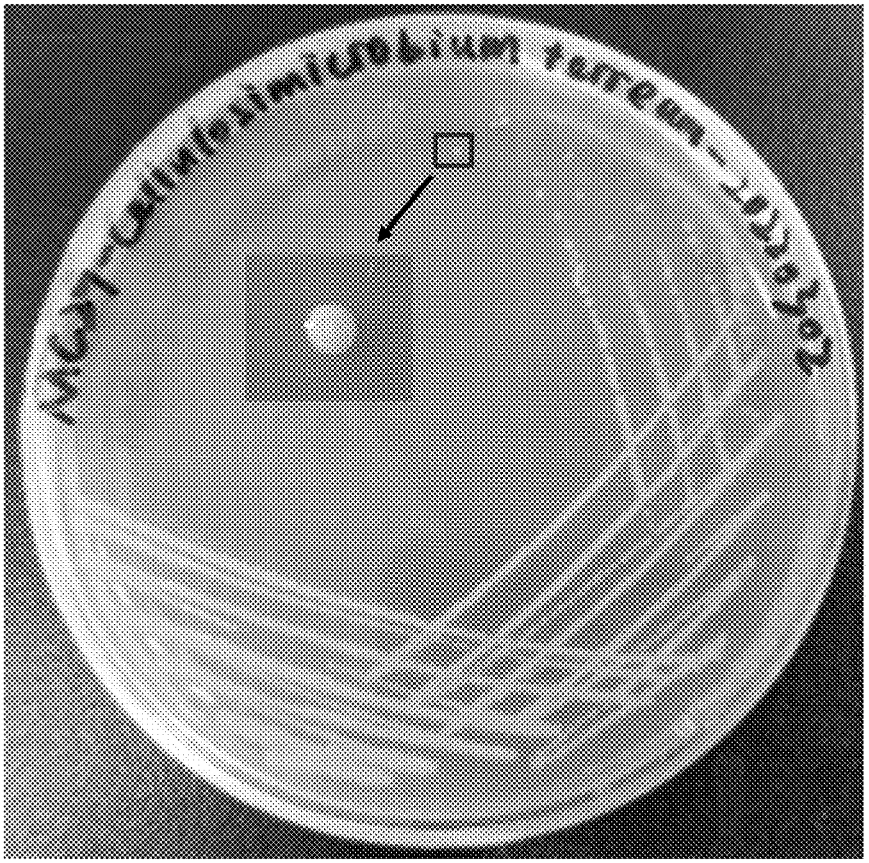
FIG. 2 shows a colony form of the *Cellulosimicrobium cellulans* MC29-GFP.

As shown in FIG. 2, the *Cellulosimicrobium cellulans* strain MC29-GFP had yellow colonies with a smooth, moist surface and neat edges, and the colonies were irregularly arranged and densely distributed. Individual strains were rod-shaped without flagella.

Physiological and biochemical experiments were conducted on the strain MC29-GFP, including: Gram staining, methyl red reaction, gelatin liquefaction experiment, catalase experiment, nitrate reduction experiment, V-P experiment, starch hydrolysis experiment, citrate utilization experiment, and aerobic experiment. The specific experimental results were shown in FIG. 3 and Table 1.

TABLE 1

Physiological and biochemical characteristics of strain MC29-GFP

| Test item | Results | Test item | Results |
|---|---|---|---|
| Gram staining | + | Citrate utilization | − |
| MR experiment | + | Gelatin liquefaction | + |
| V-P experiment | − | Aerobic experiment | Facultative anaerobic |
| With or without flagella | None | Catalase experiment | + |
| Starch hydrolysis | − | Nitrate reduction | + |

Figure 3:
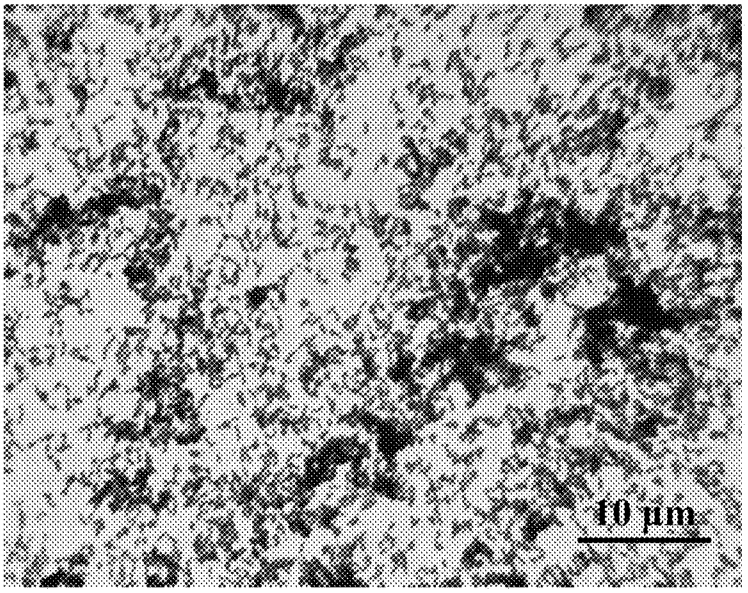
FIG. 3 shows a Gram staining image of the *Cellulosimicrobium cellulans* MC29-GFP.

As shown in FIG. 3 and Table 1, MC29-GFP was a Gram-positive bacterium. In the methyl red reaction, gelatin liquefaction experiment, catalase experiment, and nitrate reduction experiment, the strain all showed positive reactions. In the V-P experiment, starch hydrolysis experiment, and citrate utilization experiment, the strain all showed negative reactions. In the aerobic experiment, it was proved that the strain was a facultative anaerobic bacterium.

Figure 4:
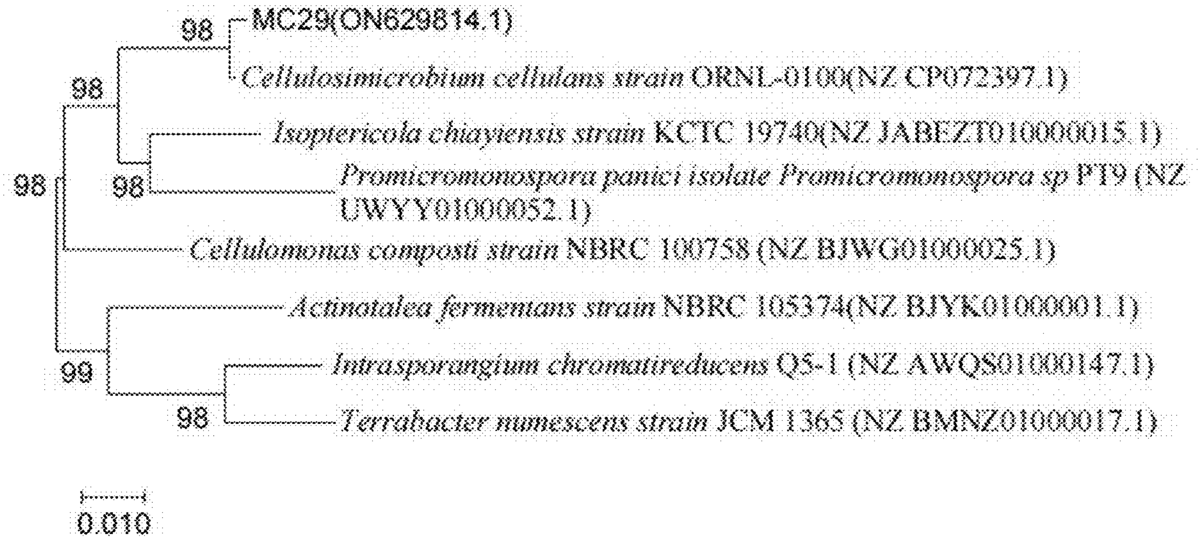
FIG. 4 shows a phylogenetic tree constructed by MEGA-X.
Figure 5A:
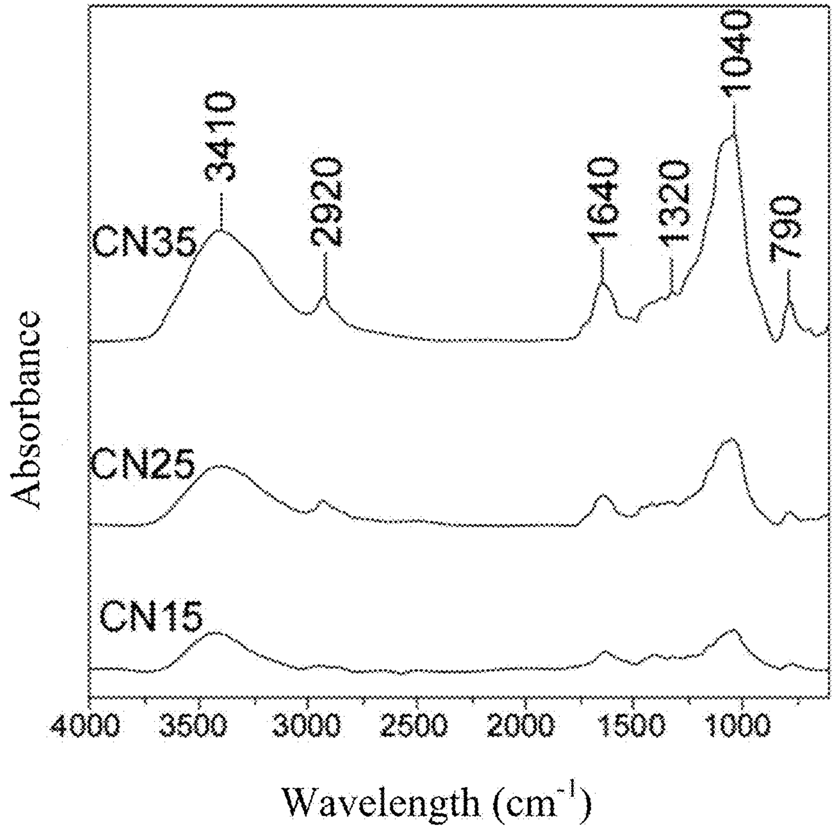
FIGS. 5A-F show infrared spectrum effects of different bacterial solutions on a straw decomposition degree under a C/N ratio for 7 d and 60 d (where
Figure 5B:
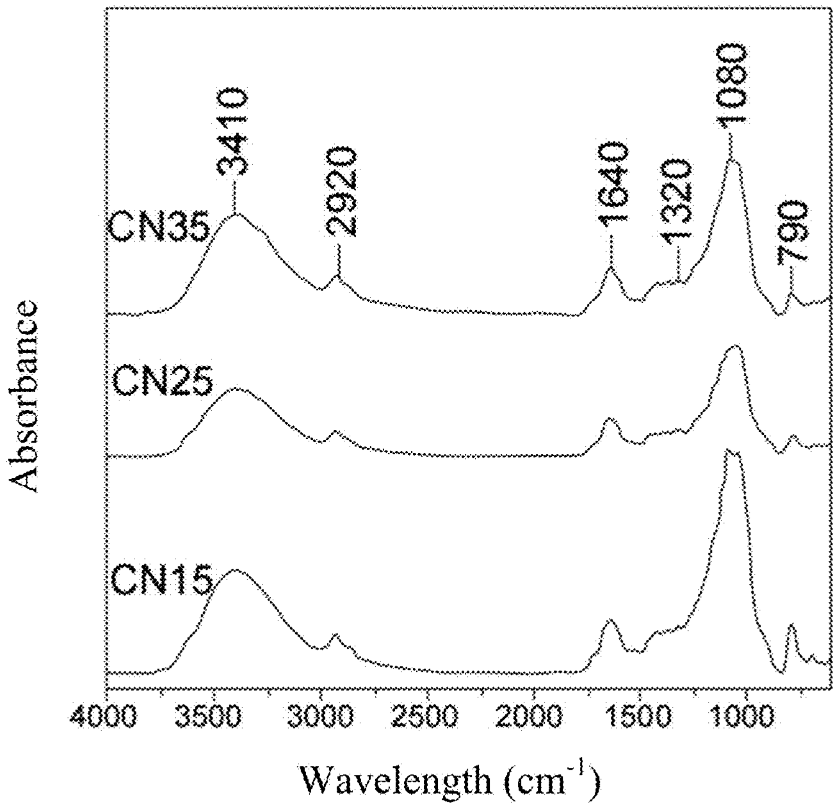
Figure 5C:
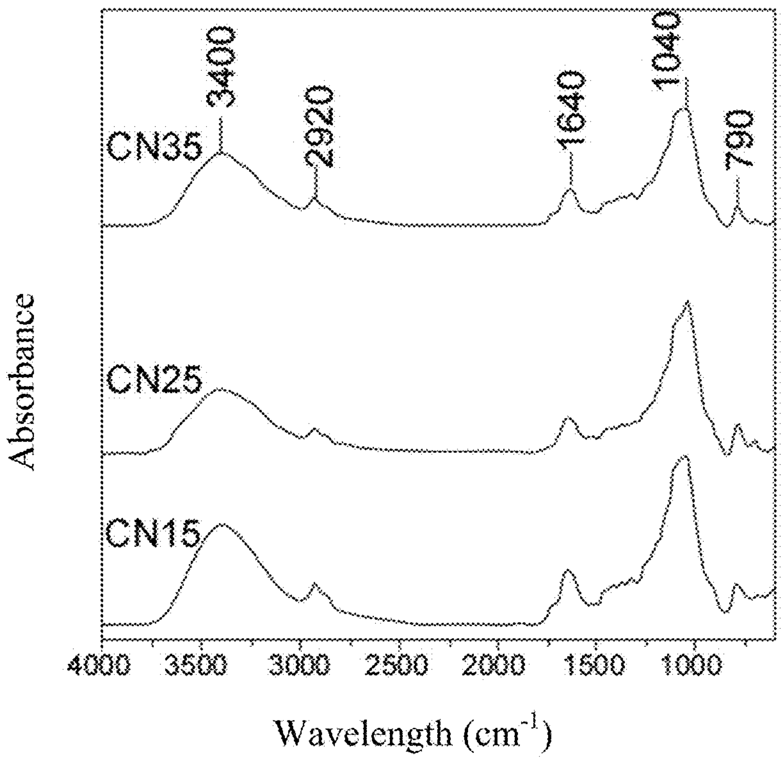
Figure 5D:
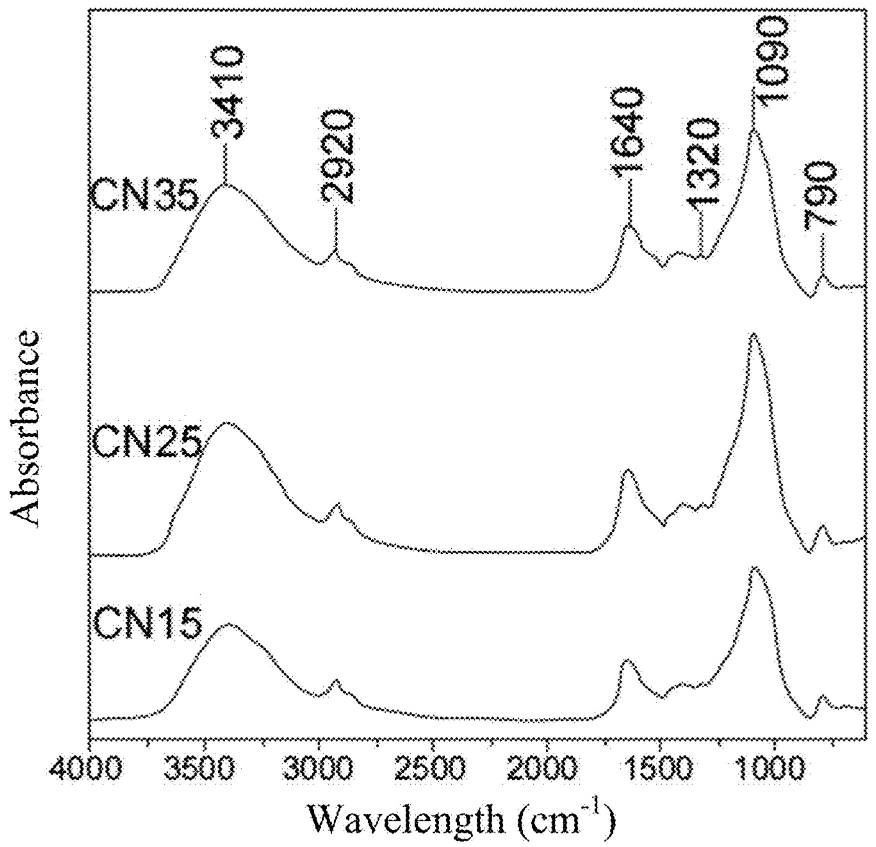
Figure 5E:
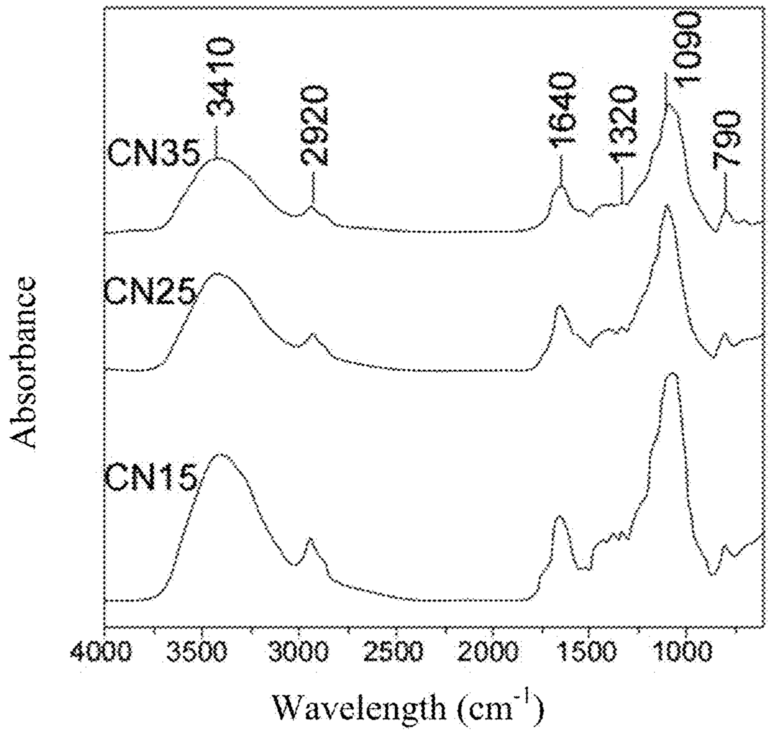
Figure 5F:
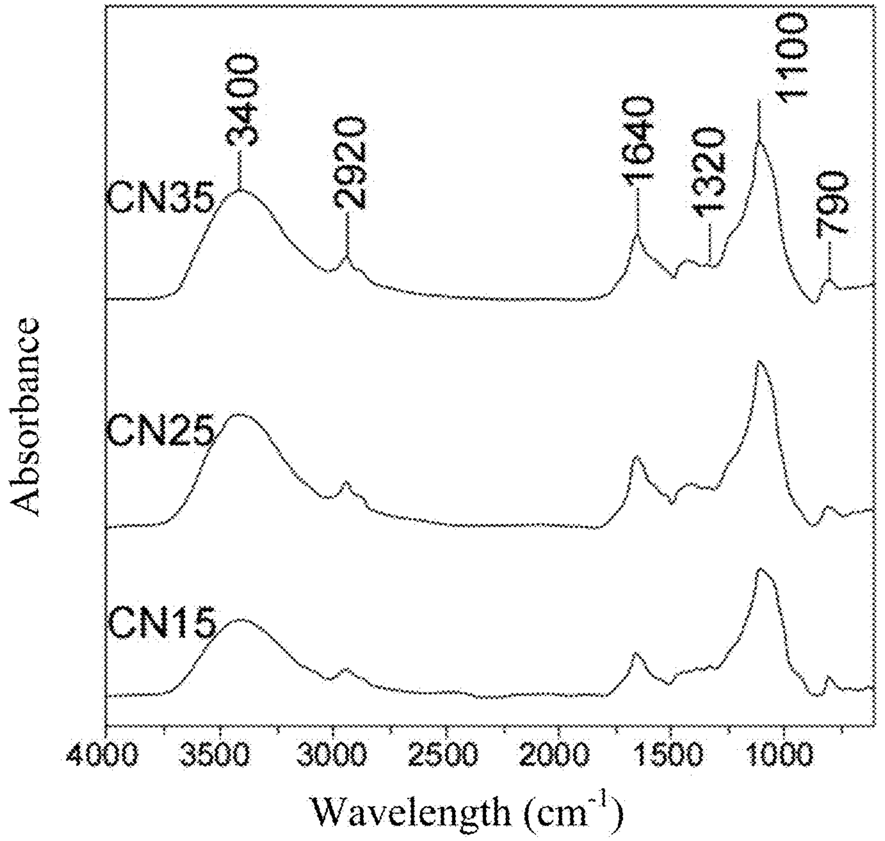

A 16S rRNA sequence of the strain MC29-GFP was searched by Blast in the NCBI database for homologous sequence alignment, and a phylogenetic tree was constructed using MEGA-X to determine the species and genus of the strain. As shown in FIG. 4, the strain MC29-GFP had a homology of up to 99% with *Cellulosimicrobium cellulans*. Therefore, according to the characteristic results of physiological, biochemical, and morphological analysis, the strain MC29-GFP was identified as *Cellulosimicrobium cellulans*.

Example 2

Preparation of a Bacterial Solution of *Cellulosimicrobium cellulans* Strain MC29-GFP (1) Preparation of reagents: an LB medium included 10 g peptone, 5 g yeast extract, 10 g sodium chloride, and 1,000 mL distilled water, adjusted to a pH value of 7.0 to 7.2, and sterilized at 121° C. for 20 min.

(2) Preparation of a seed liquid: the *Cellulosimicrobium cellulans* strain MC29-GFP stored at low temperature was inoculated into 100 mL of the liquid LB medium in a 250 mL Erlenmeyer flask, and cultured overnight in a shaking incubator until turbid. The shaking incubator had parameters: 36° C., 180 r/min.

(3) Preparation of a bacterial solution: 250 mL of a liquid LB medium was prepared in a 500 mL Erlenmeyer flask and sterilized. 2.5 mL of the seed liquid of the *Cellulosimicrobium cellulans* strain MC29-GFP was inoculated into the liquid LB medium. The shaking culture was conducted overnight in the shaking incubator until the bacterial solution was turbid, where parameters of the shaking incubator were the same as above.

(4) Bacteria washing: the bacterial solution was dispensed into 50 mL centrifuge tube, and centrifuged in a centrifuge at 8,000 r/min, 4° C. for 5 min. The sterile water was added, and the above operations were repeated 2 to 3 times, to obtain a purified bacterial solution.

(5) Determination of OD value: the purified bacterial solution was diluted 5 times, 10 times, and 20 times separately in test tubes filled with 9 mL of sterile water. The OD value was determined (a dilution factor whose OD value range was 0 to 1 was used as a reasonable dilution factor). The OD value was compared with the existing data to obtain a concentration of the purified bacterial solution at the dilution factor. According to an original volume of the purified bacterial solution, the total number of bacteria in the purified bacterial solution was obtained. The *Cellulosimicrobium cellulans* strain had a cell concentration of $2.07\times10^9$ cfu/mL.

Example 3

Composting of *Cellulosimicrobium cellulans* Strain MC29-GFP 10 cm rice straw was stacked to a height of 1 m according to the standard of 6 m in length and 4 m in width, a first layer of micro-spray belt was laid, and the pile was watered until a mass ratio of water to straw was 0.5. The UAN solution was added to adjust a C/N ratio to 35/1, 0.1% of the bacterial solution of *Cellulosimicrobium cellulans* strain MC29-GFP obtained in Example 2 was added, and a small amount of water was sprayed. The straw was stacked to a height of 1.8 m, a second layer of micro-spray belt was laid, and the pile was watered until the mass ratio of water to straw was 0.6, and micro-spraying was continued with water for 6 h.

When the temperature of the straw rose to 60° C. and the water content was 55%, the first turning over of pile was conducted. When the temperature of the straw exceeded 60° C. and the water content was lower than 40%, the second turning over of pile was conducted, such that the water content of the material pile was controlled within the range of 55% to 65%, and the temperature was controlled below 60° C. Composting was conducted for 30 d, when an oxygen content was lower than 8%, the compost should be turned over and sprayed with water in time according to the humidity. After composting for 60 d, a straw organic fertilizer was obtained.

Comparative Example 1

Preparation of Bacterial Solution and Composting of *Bacillus amyloliquefaciens* SQR9

The *Bacillus amyloliquefaciens* SQR9 was deposited in the CGMCC with a deposit number of CGMCC NO. 5808.

The preparation method of the bacterial solution of *Bacillus amyloliquefaciens* SQR9 was the same as that in Example 2, and a cell concentration of *Bacillus amyloliquefaciens* SQR9 was $1.12\times10^{9}$ cfu/mL.

The composting was the same as that in Example 3.

Experimental Example 1

Effects of Different Bacterial Solutions and Different C/N Ratios on the Decomposing Effect Of Straw Experiment site: Lujiang County, Hefei City, Anhui Province, which had a subtropical humid monsoon climate. This region showed four distinct seasons, abundant rainfall and sufficient sunlight, with an average annual temperature of 15.8° C., an average annual precipitation of 1,188 mm, more than 2000 h of sunshine, and a frost-free period of 238 d. The soil used in the test was a paddy soil with a pH of 5.29, an organic matter of 10.31 g/kg, alkaline nitrogen of 55.70 mg/kg, available phosphorus of 26.47 mg/kg, and available potassium of 35.98 mg/kg. A cropping system was rice-wheat crop rotation.

Test Setup:

1. Preparation of Raw Materials
   (1) The bacterial solution of the *Cellulosimicrobium cellulans* strain MC29-GFP obtained in Example 2 and the bacterial solution of *Bacillus amyloliquefaciens* SQR9 obtained in Comparative Example 1. The straw was rice straw that had been degraded for 0.5 to 1 weeks in a natural environment and had formed its own degrading microflora, with total carbon of 374.98 g/kg, total nitrogen of 12.93 g/kg, total phosphorus of 0.80 g/kg, and total potassium of 8.93 g/kg.
   (2) Group setting: 9 treatments: carbon-nitrogen ratio gradient (CN15:15/1, CN25:25/1, CN35:35/1)×species of stalk-decomposing bacteria (CK, SQR9, and MC29-GFP), 3 repetitions in each group, while CK was added with sterile water.
2. Test Method
   (1) Stacking of straw: 9 strip stacks of straw were stacked (with a diameter of 1 m, a height of 1 m, a weight about 54.64 kg, and a water content of about 200%), and drainage ditches with a width of 20 cm and a depth of 30 cm were dug around each stack. 18 200-mesh nylon bags containing 10 g of straw with a length of 1 cm were placed into the middle of each strip stack.
   (2) Application of nitrogen fertilizer: according to the C and N contents of wheat straw, the C/N ratio was adjusted with UAN solution (CN15:15/1, CN25:25/1, CN35:35/1).
   (3) Inoculation of strains: each pile of straw (54.64 kg) was inoculated (the bacterial solution of the *Cellulosimicrobium cellulans* strain MC29-GFP obtained in Example 2 and the bacterial solution of *Bacillus amyloliquefaciens* SQR9 obtained in Comparative Example 1). According to a total amount of $5.97\times10^{8}$ cfu, a certain amount of purified bacterial solution was evenly sprayed on each pile of straw with a sterilized watering can, and then composted according to the method for composting in Example 3.
3. Sample Collection and Index Determination Under normal management, composting was conducted for 60 d, and samples are collected on the 1st day, 7th day, 15th day, 30th day, and 60th day. According to the results, the samples on the 7th day and the 60th day were selected to determine the chemical composition of straw, the activity of lignocellulose-degrading enzymes, and the composition and structure of straw-degrading bacterial community.

4. Analysis of Chemical Composition of Straw

The straw was pressed into pieces by KBr, and the infrared spectrum analysis was conducted with a Nicolet 8700 Fourier Transform Infrared Spectrometer (Fourier Transform Infrare Spectrometer, FTIR, American Thermo Electron Corporation), with a spectrum range (4000 to 400 $cm^{-1}$) and a resolution of 4 $cm^{-1}$ by scanning in transmission mode 32 times. Before tabletting, 300 mg of pre-dried potassium bromide and 3 mg of straw samples were fully ground in an agate mortar, dried in an oven at 100° C. for about 5 min, and taken out and continued to be ground for about 30 s for molding and tabletting.

The results were shown in FIGS. 5A-F, when the straw cellulose and hemicellulose were decomposed for 7 d, the absorption peak intensities of straw cellulose and hemicellulose treated with MC29-GFP were generally lower than those of CK and SQR9. The absorption peak intensities of cellulose and hemicellulose had no significant difference between different carbon-nitrogen ratios under CK treatment, the lowest value was at CN15 under SQR9 treatment, and the lowest value was at CN25 under MC29-GFP treatment. When decomposed to 60 d, there was no significant difference in the absorption peak intensity of straw cellulose among the treatments of different strains. The general law of absorption peak intensity of straw lignin was MC29-GFP<SQR9<CK, and CN25 had the lowest value under MC29-GFP treatment. It was seen that the inoculation of MC29-GFP strain and the adjustment of CN to 25 were most conducive to the straw field composting of rice.

5. Determination of Enzyme Activity of Straw (1) Determination of Straw Cellulase (CL) Activity The CL activity in the collected samples was measured by the anthrone colorimetric method. Definition of enzyme activity: an amount of enzyme needed to catalyze the production of 1 μg of glucose per milligram of tissue protein per minute was defined as 1 enzyme activity unit, namely g/min/mg.

Figure 6A:
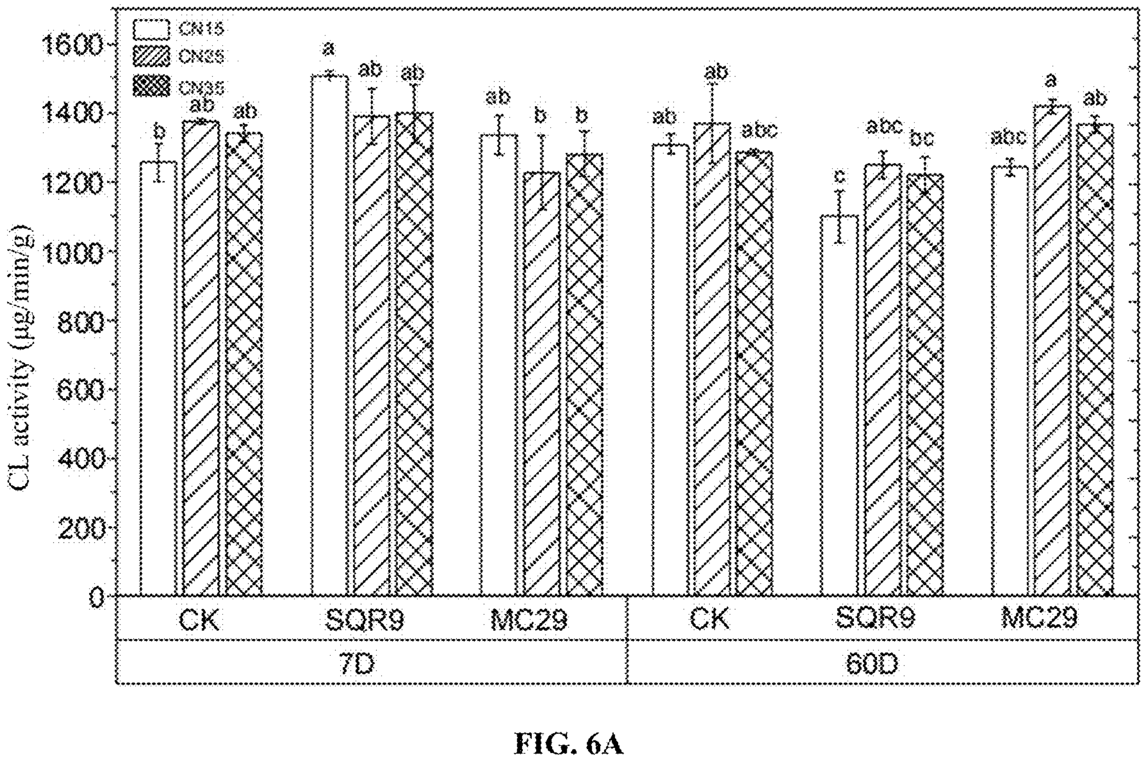
FIGS. 6A-B show changes in an enzyme activity of straw under different C/N ratios and bacterial solutions

The results were shown in FIG. 6A, different bacterial agents had different effects on CL activity. After 60 d of decomposition, the CL activity of CN25 was the highest among CK and SQR9 treatments, and the CL activity of MC29-GFP was significantly higher than that of CK and SQR9. The enzyme activities were 1416.95 μg/min/mg, 1362.07 μg/min/mg, and 1248.55 g/min/mg, respectively.

(2) Determination of Straw Lignin Peroxidase (LiP) Activity

The activity of LiP in the collected samples was determined by the method of oxidation rate of veratryl alcohol. Definition of enzyme activity: an amount of enzyme required to oxidize 1 nmol of veratryl alcohol per minute per mg of protein was 1 enzyme activity unit (U), namely nmol/min/mg.

Figure 6B:
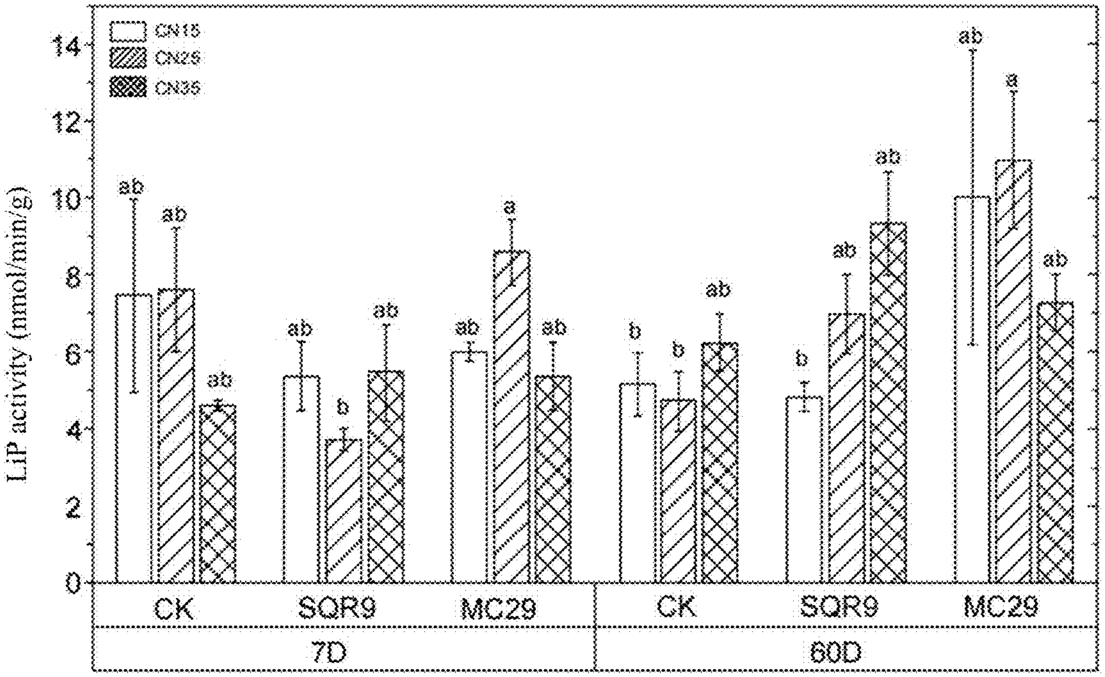

The results were shown in FIG. 6B, different bacterial agents had different effects on the LiP activity. When it was decomposed to 60 d, the LiP activity was the highest in CN35 in CK and SQR9 treatments, at 6.21 nmol/min/mg and 9.34 nmol/min/mg, respectively. In MC29-GFP treatment, the LiP activity of CN25 was the highest, at 10.98 nmol/min/mg.

6. Dynamic Changes in the Composition and Structure of the Microbial Community of Straw Under Different Treatments (1) DNA Extraction and PCR Amplification According to the E.Z.N.A.® Soil DNA Kit (Omega Bio-tek, Norcross, GA, U.S.) kit instructions, the total DNA of the microbial groups in the straw samples was extracted. The study of the bacterial community structure used the primers 799F (upstream primer) 5'-AACMGGATTAGATACCCKG-3' (SEQ ID NO:1) and 1115R (downstream primer) 5'-AGGGTTGCGCTCGTTG-3' (SEQ ID NO:2) of V4 to V5 regions of the 16s rRNA for PCR amplification, and the amplification primers for each sample contained an 8-base tag sequence to differentiate the samples.

A 20 μL PCR reaction system was prepared, including: 4 μL of 5× FastPfu Buffer, 2 μL of 2.5 mM dNTPs, 0.8 μL for each of upstream and downstream primers (5 μM), 0.4 μL of FastPfu Polymerase, and 10 ng of template DNA. A PCR amplification program was as follows: 94° C. for 4 min; 94° C. for 30 s, 55° C. for 30 s, and 72° C. for 1 min, conducting 25 cycles; and 72° C. for 10 min. An amplified product was subjected to 2% agarose gel electrophoresis, and purified using an AxyPrep DNA Gel Extraction Kit (Axygen Biosciences, Union City, CA, U.S.) kit according to the operating procedures in the manual.

(2) Library Construction and Sequencing

Qubit®3.0 (Life Invitrogen) was used to accurately quantify the purified PCR product, and then 24 amplicon samples with different tag sequences were mixed in equal amounts. The DNA products after pooling were used to construct an Illumina paired-end sequencing PE library according to a construction process of the Illumina genome sequencing library. The amplicon library was sequenced in PE250 mode on an Illumina platform according to the standard procedure, and the library construction and sequencing were undertaken by Shanghai BIOZERON Co., Ltd. Raw data had been uploaded to the NCBI SRA database.

(3) Preprocessing of Sequencing Data

The raw data obtained by sequencing distinguished samples according to the barcodes and primers at the beginning and end of the sequence, and adjusted the direction of the sequence. After the data was split, the data was cleaned of impurities. The parameter requirements were as follows: (i) the bases with a quality value below 20 at the end of the read were filtered, and a window of 10 bp was set. If the average quality value in the window was lower than 20, the back-end bases were cut off from the window, and the reads below 50 bp after the quality control were filtered. (ii) The maximum mismatch ratio allowed in the overlap region of the spliced sequence was 0.2, and non-conforming sequences were removed. (iii) According to the overlap relationship between PE reads, the paired reads were spliced (merged) into a sequence, and the minimum overlap length was 10 bp.

After the original data was subjected to high-grade quality control and removal of chimeras, valid data were obtained. According to different similarity levels, all sequences in the valid data were classified to obtain operational taxonomic units (OTUs).

UCHIME software was used to identify and remove chimeric sequences, and UPARSE (version 7.1, available from drive5.com) software was used to cluster sequences with a similarity of 97% into OTUs. The Bayesian algorithm of RDP classifier (available from rdp.cme.msu.edu) was used to conduct taxonomic analysis on OTU representative sequences, compared with the Silva database, and the confidence threshold was 0.7. Finally, the species information of each OTU at each taxonomic level was obtained, and the microbial community composition of each sample at each taxonomic level was counted accordingly.

According to the classification standard of rare bacteria whose relative abundance was less than 1%, the phyla with a relative abundance of less than 1% in each sample were discarded. At the taxonomic level of the phylum, CK, SQR9, and MC29-GFP were distributed in 9 known bacterial phyla at different times (the unclassified Bacterial phyla, the Bacterial phyla without clear taxonomic information at the taxonomic level, or the Bacterial phyla with very low names and relatively low abundances were classified as "others").

Figure 7A:
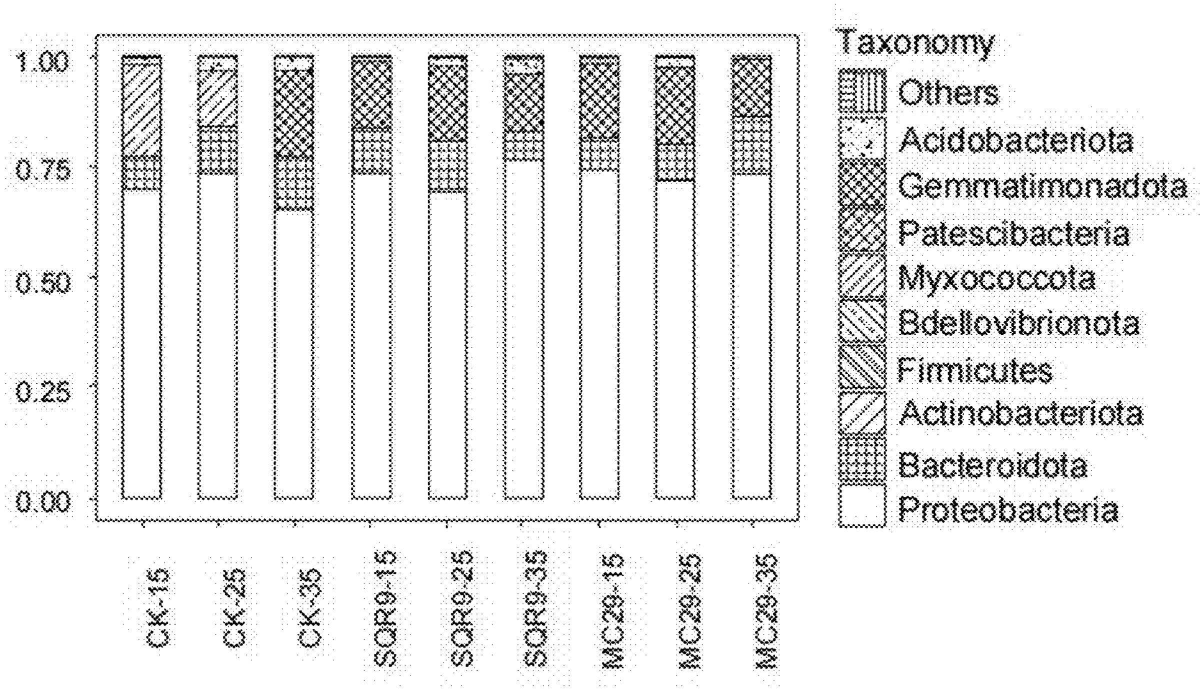
FIGS. 7A-B show relative abundance of dominant microflora at a Phylum level under different treatments (FIG. 7A, a relative abundance of the dominant microflora at 7 d.
Figure 7B:
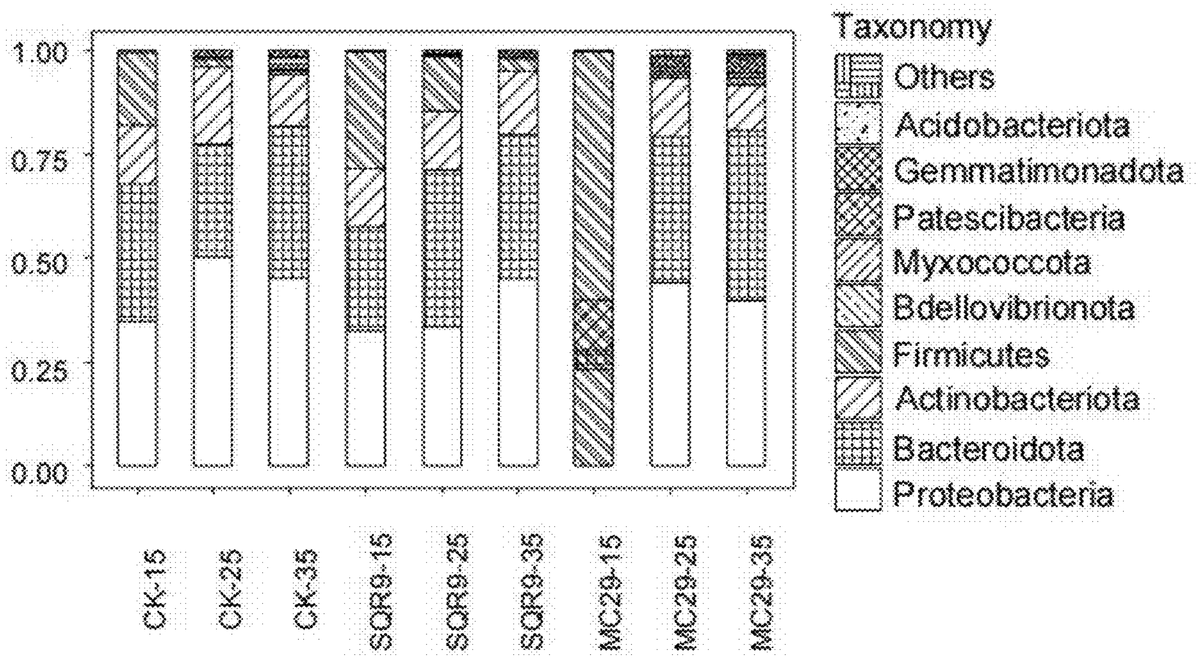

As shown in FIGS. 7A-B, when the decomposition time was 7 d, Proteobacteria had the highest relative abundance under different treatments, which was the main dominant microflora, followed by Bacteroidota and Actinobacteriota. However, with the prolongation of the decomposition time, when the decomposition time was 60 d, the relative abundance of Proteobacteria gradually decreased, while the relative abundance of Bacteroidota and Firmicutes increased. The four phyla of Proteobacteria, Bacteroidota, Actinobacteriota, and Firmicutes had higher relative abundance. Patescibacteria, Myxococcota, Bdellovibrionota, Gemmatimonadota, and Acidobacteriota and other bacterial phyla had lower relative abundance in each sample.

At 7 d of composting, compared with CK and SQR, the relative abundance of Proteobacteria was generally higher under MC29-GFP treatment, and the relative abundance of Firmicutes was generally lower. At 60 d of composting, the relative abundance of Proteobacteria, Bacteroidota, and Actinobacteriota under MC29-GFP treatment was generally lower than that of CK and SQR9, while the relative abundance of Firmicutes was generally higher than that of CK and SQR9. Most lignocellulose-degrading bacteria belong to Proteobacteria, and their high abundance indicates a strong degradation ability. In summary, MC29-GFP enhances straw degradation ability through direct degradation and optimization of degrading microflora.

Experimental Example 2

Influence of Different Fertilizers on Yield and Quality of Rice

Experiment site: Zesheng Family Farm in Suxiao Township, Feixi County, Hefei City, Anhui Province, which had a subtropical humid monsoon climate. This region showed four distinct seasons, abundant rainfall and sufficient sunlight, with an average annual temperature of 15.8° C., an average annual precipitation of 1,188 mm, more than 2000 h of sunshine, and a frost-free period of 238 d. The soil used in the test was a paddy soil with a surface soil pH of 5.31, an organic matter of 31.39 g/kg, available nitrogen of 190.32 mg/kg, available phosphorus of 22.26 mg/kg, and available potassium of 238.4 mg/kg.

Test Setup:

The test crop was rice, and there were 4 treatments in the test, namely:

(1) Treatment 1 (T1): no fertilization.

(2) Treatment 2 (T2): conventional fertilization (base fertilizer: 15-15-15 common compound fertilizer, 600 $kg/hm^2$, topdressing urea 150 $kg/hm^2$ at tillering stage, topdressing urea 112.5 $kg/hm^2$ at booting stage).

(3) Treatment 3 (T3): straw organic fertilizer in Example 3+85% conventional fertilization (base fertilizer: 250 $kg/hm^2$ of straw organic fertilizer in Example 3, 450 kg/hm$^2$ of 15-15-15 common compound fertilizer, topdressing urea 120 kg/hm$^2$ at tillering stage, topdressing urea 105 kg/hm$^2$ at booting stage).

(4) Treatment 4 (T4): Laimjia straw organic fertilizer purchased on the market+85% conventional fertilization (base fertilizer: 250 kg/hm$^2$ of Laimjia straw organic fertilizer purchased on the market, 450 kg/hm$^2$ of 15-15-15 common compound fertilizer, topdressing urea 120 kg/hm$^2$ at tillering stage, topdressing urea 105 kg/hm$^2$ at booting stage).

Each treatment was repeated 3 times, with an area of 2.5×8 m$^2$, arranged in random blocks. A ridge of 0.5 m was set up between each plot and wrapped with plastic film; each treatment was single-irrigated in a single row to prevent water and fertilizer from flowing; protective lines were set up around the plot. Other field managements were conducted according to the habits of local farmers. When harvesting, the yield, yield composition, protein content, and amylose content of each group were counted. Specific results are shown in Table 2.

The protein content and amylose content of rice were determined by FOSS1241 near-infrared grain analyzer.

TABLE 2

Effects of partial substitution of chemical fertilizers by straw organic fertilizer on rice yield, yield composition, and main quality characteristics

| Treatment | Plant height (cm) | Number of productive ears (×10$^5$/hm$^2$) | Grain number per panicle (/grains per panicle) | Thousand-grain weight (g) | Actual output (kg/hm$^2$) | Protein (%) | Amylose content (%) |
|---|---|---|---|---|---|---|---|
| T1 | 82.3 ± 5.2b | 24.0 ± 3.0b | 108.5 ± 10.2c | 22.1 ± 1.2a | 7764.0 ± 321.0c | 9.4 ± 0.3c | 20.9 ± 1.2a |
| T2 | 96.3 ± 6.1a | 34.5 ± 6.0a | 132.6 ± 4.4b | 22.6 ± 1.4a | 10254.0 ± 502.5b | 10.5 ± 0.6b | 19.7 ± 1.4a |
| T3 | 97.0 ± 6.9a | 36.0 ± 4.5a | 146.8 ± 5.1a | 22.8 ± 2.0a | 11365.5 ± 618.0a | 11.8 ± 0.6a | 17.2 ± 0.9b |
| T4 | 91.3 ± 6.7ab | 31.5 ± 3.0a | 129.1 ± 9.2b | 22.2 ± 1.9a | 10108.5 ± 828.0b | 10.6 ± 0.4b | 19.4 ± 1.2a |

As shown in Table 2, different treatments had little effect on the thousand-grain weight of rice, and none of them reached a significant level. Compared with T1, the plant height, productive panicle number per mu, grain number per panicle, and yield of rice treated with T2 were significantly increased by 17.8%, 50.0%, 21.5%, and 45.4%, respectively. The number of grains per panicle and yield of T3 treatment were significantly increased by 7.7% and 10.8% compared with T2. Compared with T4 treatment, the number of grains per panicle and yield of T3 treatment were significantly increased by 10.6% and 12.4%. The results showed that the application of bio-organic fertilizers under the condition of reducing chemical fertilizers by 20% could increase rice yield, mainly because of the increase of rice panicle number. There were significant differences in protein content and amylose content of rice among different treatments. Compared with T1, T2 and T4, the rice of T3 treatment had significantly increased protein content by 25.5%, 12.4%, and 11.3%, respectively, and had significantly decreased amylose content by 17.7%, 12.7%, and 11.3%. The results showed that the application of the straw organic fertilizer of the present disclosure could significantly improve the quality of rice.

The above are merely preferred implementations of the present disclosure. It should be noted that several improvements and modifications may further be made by a person of ordinary skill in the art without departing from the principle of the present disclosure, and such improvements and modifications should also be deemed as falling within the protection scope of the present disclosure.

What is claimed is:

1. A method for quickly decomposing straw in field, comprising the following steps: adjusting the straw to a carbon/nitrogen (C/N) ratio of (25-35): 1, mixing the straw with a bacterial solution, and conducting composting;

wherein a method for preparing the bacterial solution comprises the following steps: inoculating *Cellulosimicrobium cellulans* strain into an LB medium to prepare a seed liquid, inoculating the seed liquid into a liquid LB medium, and conducting culture to obtain a bacterial solution; wherein the bacterial solution has the *Cellulosimicrobium cellulans* strain at a concentration of $1.0\times10^9$ cfu/mL to $2.5\times10^9$ cfu/mL;

wherein the *Cellulosimicrobium cellulans* strain is named *Cellulosimicrobium cellulans* MC29-GFP, and is deposited in the China General Microbiological Culture Collection Center (CGMCC), with a deposit number of CGMCC No. 25013.

2. The method according to claim 1, wherein the C/N ratio of the straw is adjusted by adding a nitrogen source; and the nitrogen source is a urea ammonium nitrate (UAN) solution.

3. The method according to claim 1, wherein the composting is conducted for 57 d to 63 d.

* * * * *

SEQUENCE LISTING

```
Sequence total quantity: 2
SEQ ID NO: 1           moltype = DNA  length = 19
FEATURE                Location/Qualifiers
source                 1..19
                       mol_type = other DNA
                       note = upstream primer
                       organism = synthetic construct
```

-continued

```
SEQUENCE: 1
aacmggatta gataccckg                                          19

SEQ ID NO: 2            moltype = DNA  length = 16
FEATURE                 Location/Qualifiers
source                  1..16
                        mol_type = other DNA
                        note = downstream primer
                        organism = synthetic construct
SEQUENCE: 2
agggttgcgc tcgttg                                             16
```